(12) United States Patent
Slattery et al.

(10) Patent No.: US 11,338,115 B2
(45) Date of Patent: May 24, 2022

(54) FINNED ANGIOPLASTY BALLOON

(71) Applicant: Merit Medical Ireland Limited, Dublin (IE)

(72) Inventors: David Slattery, Kinavara (IE); John Joseph Kelly, Naas (IE); Jonathan Akehurst, Armagh (GB); John Paul Culloty, Castleisland (IE); Tomás Christopher Brosnan, Castleisland (IE); David Fleming, Killarney (IE)

(73) Assignee: Merit Medical Ireland Limited

( * ) Notice: Subject to any disclaimer, the term of this patent is extended or adjusted under 35 U.S.C. 154(b) by 202 days.

(21) Appl. No.: 16/337,650

(22) PCT Filed: Sep. 29, 2017

(86) PCT No.: PCT/EP2017/074852
§ 371 (c)(1),
(2) Date: Mar. 28, 2019

(87) PCT Pub. No.: WO2018/060466
PCT Pub. Date: Apr. 5, 2018

(65) Prior Publication Data
US 2019/0344054 A1    Nov. 14, 2019

(30) Foreign Application Priority Data
Sep. 30, 2016 (EP) .................................... 16191981

(51) Int. Cl.
*A61M 25/10* (2013.01)
*A61B 17/3207* (2006.01)
*A61B 17/22* (2006.01)

(52) U.S. Cl.
CPC ... *A61M 25/104* (2013.01); *A61B 17/320725* (2013.01); *A61M 25/1002* (2013.01);
(Continued)

(58) Field of Classification Search
CPC . A61B 17/320725; A61B 2017/22001; A61M 2025/1086
See application file for complete search history.

(56) References Cited

U.S. PATENT DOCUMENTS 5,653,690 A * 8/1997 Booth .................. A61M 25/04
604/103.07
5,976,181 A * 11/1999 Whelan .................. A61F 2/958
606/194

(Continued)

FOREIGN PATENT DOCUMENTS

| EP | 0442657 | 8/1991 |
| WO | 2015077545 | 5/2015 |

OTHER PUBLICATIONS

Office Action dated May 14, 2020 for U.S. Appl. No. 15/735,556.
(Continued)

*Primary Examiner* — Alexander J Orkin
(74) *Attorney, Agent, or Firm* — Dorsey & Whitney LLP

(57) ABSTRACT

An angioplasty balloon (1) comprises an elongate tube (16) having a relaxed delivery configuration and an expanded deployed configuration. The elongate tube (16) comprises a proximal neck portion (10), a distal neck portion (8), a main body region, a tapered proximal portion (11) extending between the main body region and the proximal neck portion (10); and a tapered distal portion (9) extending between the main body region (3) and the distal neck portion (8), the elongate tube has only three fins (4, 5, 6) which are integrally formed with the tube and which are spaced equidistant from one another about the exterior of the tube. The fins (4, 5, 6) project radially outwardly from the exterior surface of the tube and the fins (4, 5, 6) extending longitudinally only along part of the main body region (3), resulting in the end-sections of the balloon main body being fin-free.

19 Claims, 7 Drawing Sheets

(52) U.S. Cl.
CPC .............. *A61B 2017/22001* (2013.01); *A61M 2025/109* (2013.01); *A61M 2025/1079* (2013.01); *A61M 2025/1086* (2013.01)

(56) References Cited

U.S. PATENT DOCUMENTS

| | | | |
|---|---|---|---|
| 6,251,109 B1* | 6/2001 | Hassett | A61B 18/1492 |
| | | | 606/45 |
| 6,544,222 B1* | 4/2003 | Yang | A61F 2/958 |
| | | | 604/103.01 |
| 6,884,257 B1 | 4/2005 | Cox | |
| 2002/0010489 A1* | 1/2002 | Grayzel | A61F 2/958 |
| | | | 606/194 |
| 2003/0144683 A1 | 7/2003 | Sirhan et al. | |
| 2004/0133223 A1* | 7/2004 | Weber | A61F 2/91 |
| | | | 606/159 |
| 2004/0215223 A1 | 10/2004 | Shaw et al. | |
| 2005/0038383 A1 | 2/2005 | Kelley et al. | |
| 2005/0149082 A1* | 7/2005 | Yee | A61M 25/1002 |
| | | | 606/159 |
| 2006/0106412 A1* | 5/2006 | Crow | A61B 17/320725 |
| | | | 606/192 |
| 2006/0149308 A1* | 7/2006 | Melsheimer | A61B 17/320725 |
| | | | 606/192 |
| 2008/0015540 A1* | 1/2008 | Muni | A61B 17/3421 |
| | | | 604/500 |
| 2009/0012469 A1* | 1/2009 | Nita | A61B 17/22012 |
| | | | 604/104 |
| 2009/0105686 A1 | 4/2009 | Snow | |
| 2010/0228333 A1 | 9/2010 | Drasler et al. | |
| 2010/0286593 A1* | 11/2010 | Krolik | A61B 17/320725 |
| | | | 604/22 |
| 2011/0160756 A1* | 6/2011 | Aggerholm | A61B 17/320725 |
| | | | 606/159 |
| 2011/0270226 A1 | 11/2011 | Kocur | |
| 2012/0191111 A1* | 7/2012 | Aggerholm | A61B 17/320725 |
| | | | 606/159 |
| 2012/0277843 A1 | 11/2012 | Weber et al. | |
| 2012/0296313 A1 | 11/2012 | Adreacchi et al. | |
| 2012/0324696 A1 | 12/2012 | Liu et al. | |
| 2015/0012032 A1* | 1/2015 | Cox | A61M 25/10184 |
| | | | 606/192 |
| 2017/0080192 A1* | 3/2017 | Giasolli | B65D 19/42 |

OTHER PUBLICATIONS

European Search Report dated Oct. 19, 2016 for EP16164520.5.
International Search Report and Written Opinion dated Sep. 12, 2016 for PCT/EP2016/063398.
International Search Report and Written Opinion dated Dec. 13, 2017 for PCT/EP2017/074852.
Notice of Allowance dated Sep. 8, 2020 for U.S. Appl. No. 15/735,556.

* cited by examiner

FINNED ANGIOPLASTY BALLOON

RELATED APPLICATIONS

This application is a 371 National Stage Filing of International Application No. PCT/EP2017/074852, filed on Sep. 29, 2017 and titled, "Finned Angioplasty Balloon" which, in turn, claims priority to European Application No. 16191981.6 filed on Sep. 30, 2016, both of which are hereby incorporated by reference in their entireties.

INTRODUCTION

The present invention relates to an angioplasty balloon for a catheter and its use in scoring and dilating hardened regions of a diseased vessel.

Coronary artery disease and peripheral artery disease are both major and growing health problems throughout the world, associated with aging populations and lifestyle changes. Both diseases are characterised by atherosclerosis, which is the build-up of plaque or fatty deposits on the inside of the arteries, resulting in the arteries becoming blocked or narrowed. In the coronary arteries, this can result in reduced blood flow to and oxygenation of the heart, leading to angina and heart attack. In the peripheral arteries, this can result in reduced blood flow to the affected organs/limbs, which can have many severe consequences such as chronic limb ischemia and diabetic foot, potentially requiring amputation.

Occluded, stenotic, or narrowed blood vessels may be treated with a number of relatively non-invasive medical procedures including percutaneous transluminal angioplasty, stenting and atherectomy. Angioplasty techniques typically involve the use of a balloon dilatation catheter. The balloon dilatation catheter is advanced over a guidewire so that the balloon is positioned adjacent to a stenotic lesion. The balloon is then inflated, compressing the plaque against the vessel wall and the restriction of the vessel is opened.

One of the major limitations of traditional angioplasty in treating coronary artery disease and peripheral artery disease is re-stenosis, which is the re-narrowing of the artery post procedure. In addition, in cases where the occlusion or stenosis is severely hardened or calcified, standard angioplasty balloons alone may not be effective. Evidence has shown that in such cases, cutting or scoring the plaque at the stenosis during treatment using, for example, an angioplasty balloon equipped with cutting blades or wires, can reduce the incidence of re-stenosis and improve overall procedure success rate. Additionally, cutting or scoring the stenosis may reduce trauma to the blood vessel and/or to adjacent healthy tissue, compared to, for instance, using a high pressure balloon to force open the vessel lumen. Angioplasty balloons equipped with cutting blades or wires mounted on the balloon's external surface have been developed to address this clinical need. Known devices such as the Flextome™ cutting Balloon™ dilatation device, the AngioSculpt™ scoring balloon catheter, VascuTrak® PTA dilatation catheter and the FX-miniRail™ balloon catheter include cutting blades or wires on the external surface of the balloon.

There are however a number of problems associated with currently available cutting/scoring angioplasty balloons. The use of these devices often results in unintentional incision, perforation, or dissection of the arteries during insertion and/or withdrawal caused by the metal blades or wires, often requiring emergency treatment such as stent graft surgery. Angioscore reports that its AngioSculpt™ device has a lower dissection rate of 9.7% compared to 30% for other comparable devices. However, this clearly is still a high percentage of total cases. Secondly, cutting/scoring angioplasty balloons are also typically more difficult to advance through the vasculature to the target lesion because the metal blades/wire frames make the devices stiffer and less flexible than standard angioplasty catheters. Thirdly, these devices do not conform well to vasculature curvature due to the stiffness/rigidity of the metal blades/wire frames, resulting in sub-optimal treatment and/or risk of dissection in cases where the lesion is situated close to a curve in the vessel. Fourthly, there have been reported incidences of both blade detachment and device entrapment in previously placed stents during dilatation procedures for treating in-stent restenosis, requiring emergency procedures to retrieve the detached blade or entrapped device. Fifthly, cutting blades or wires increase the overall profile (outer diameter) of the device, requiring a larger insertion sheath than a standard angioplasty balloon, which results in greater difficulty in achieving haemostasis post procedure, longer patient recovery time and higher procedure cost. Furthermore, attaching cutting blades or wires onto the external surface of an angioplasty balloon adds significant complexity to the manufacturing process, can compromise pressure performance, and increases the cost of the device. Sixthly, fins extending along the entire length of the balloon and cone can promote melon seeding, in use. Melon seeding refers to slippage of the balloon from the target site.

US20030144683 and US20050015107A describe angioplasty balloons with integral fins of generally triangular shape in cross section.

There is an ongoing need for improved angioplasty scoring balloons and improved methods of treating intravascular stenosis and occlusions.

It is an object of the present invention to provide a novel angioplasty balloon device that seeks to alleviate at least some of the aforementioned problems.

STATEMENTS OF INVENTION

According to the invention there is provided an angioplasty balloon comprising:
 an elongate tube of polymeric material having a relaxed delivery configuration and an expanded deployed configuration, the elongate tube comprising:
  a proximal neck portion;
  a distal neck portion
  a main body portion;
  a proximal transition portion between the proximal neck portion and the main body portion;
  a distal transition portion between the distal neck portion and the main body portion,
 a plurality of radially extending fins formed integrally with the elongate tube, the fins extending longitudinally along only a part of the main body portion leaving:
  a proximal region and a distal region of the main body portion;
  the proximal transition portion and the distal transition portion; and
  the proximal neck portion and the distal neck portion, free of fins when the tube is in the expanded configuration.

Also provided is an angioplasty balloon comprising:
 an elongate tube of polymeric material having a relaxed delivery configuration and an expanded deployed configuration, the elongate tube comprising:
  a proximal neck portion;
  a distal neck portion a main body portion;
a proximal transition portion between the proximal neck portion and the main body portion;
a distal transition portion between the distal neck portion and the main body portion,
only three radially extending fins formed integrally with the elongate tube, the fins being spaced circumferentially equidistant from one another around the exterior of the tube, the fins extending longitudinally along only a part of the main body portion leaving:
a proximal region and a distal region of the main body portion;
the proximal transition portion and the distal transition portion; and
the proximal neck portion and the distal neck portion, free of fins when the tube is in the expanded configuration.

Also provided is an angioplasty balloon comprising:
an elongate tube of polymeric material having a relaxed delivery configuration and an expanded deployed configuration, the elongate tube comprising:
a proximal neck portion;
a distal neck portion
a main body portion;
a proximal transition portion between the proximal neck portion and the main body portion;
a distal transition portion between the distal neck portion and the main body portion,
a plurality of radially extending fins formed integrally with the elongate tube, the fins extending longitudinally along only a part of the main body portion leaving:
a proximal region and a distal region of the main body portion;
the proximal transition portion and the distal transition portion; and
the proximal neck portion and the distal neck portion, free of fins when the tube is in the expanded configuration
wherein the fin-free proximal region of the main body has a length $L_1$ of from 0.6 to 1.2 times the nominal diameter of the balloon and wherein the fin-free distal region of the main body has a length $L_2$ of from 0.6 to 1.2 times the nominal diameter of the balloon.

In one embodiment the fin-free proximal region of the main body has a length $L_1$ of from 0.6 to 1.2 times the nominal diameter of the balloon.

In one case the fin-free proximal region of the main body has a length $L_1$ of about 0.8 times the nominal diameter of the balloon.

In one case the fin-free proximal region of the main body has a length $L_1$ of about 0.75 times the nominal diameter of the balloon.

In one embodiment the fin-free distal region of the main body has a length $L_2$ of from 0.6 to 1.2 times the nominal diameter of the balloon.

In one case the fin-free distal region of the main body has a length $L_2$ of about 0.8 times the nominal diameter of the balloon.

In one case the fin-free distal region of the main body has a length $L_2$ of about 0.75 times the nominal diameter of the balloon.

In some embodiments the length $L_3$ of the fin preferably equals the balloon nominal length minus about one and a half times the balloon nominal diameter.

In one case the height of each of the fins is about 0.75 mm or less.

In one case the width of each of the fins, at their widest point, is about 0.5 mm or less.

In some embodiments a ratio of the height of the fin to the width of the base of the fin is from about 1.25:1 to about 1.75:1.

Also provided is an angioplasty balloon comprising:
an elongate tube of polymeric material having a relaxed delivery configuration and an expanded deployed configuration, the elongate tube comprising:
a proximal neck portion;
a distal neck portion
a main body portion;
a proximal transition portion between the proximal neck portion and the main body portion;
a distal transition portion between the distal neck portion and the main body portion,
a plurality of radially extending fins formed integrally with the elongate tube, the fins extending longitudinally along only a part of the main body portion leaving:
a proximal region and a distal region of the main body portion;
the proximal transition portion and the distal transition portion; and
the proximal neck portion and the distal neck portion, free of fins when the tube is in the expanded configuration,
wherein the fins are of generally triangular shape in transverse cross section, the height of each of the fins is about 0.75 mm or less, the width of each of the fins, at their widest point, is about 0.5 mm or less and wherein a ratio of the height of the fins to the width of the base of the fins is from about 1.25:1 to about 1.75:1.

In some embodiments the length $L_3$ of the fin equals the balloon nominal length minus about one and a half times the balloon nominal diameter.

The fins are preferably spaced equidistant from one another around the exterior of the tube.

Preferably the angioplasty balloon consists of only three fins.

A distal end of each fin is preferably of generally concave shape in longitudinal cross section.

A proximal end of each fin is preferably of generally convex shape in longitudinal cross section.

In some cases the tips of the fins are rounded.

In preferred embodiments the fins are of generally triangular shape in transverse cross section.

The fins may have longitudinally spaced-apart interruptions.

The tube may be of Nylon material, such as Nylon 12.

The invention also provides an angioplasty system comprising an angioplasty balloon of the invention and a catheter to which the balloon is mounted, the catheter comprising an outer shaft to which a proximal end of the balloon is mounted and an inner shaft which extends through the balloon.

In preferred embodiments the inner tube has at least one radiopaque marker band thereon aligned with the fin-free proximal or distal region of the main body portion of the balloon.

In one embodiment the inner tube has a distal marker band aligned with the fin-free distal region of the main body portion of the balloon and a proximal marker band aligned with the fin-free proximal region of the main body portion of the balloon.

The invention further provides a method of treating a region of stenosis in a vasculature comprising the steps of:
providing an angioplasty system;
advancing the catheter to a lesion;

with the balloon in the relaxed configuration, advancing the catheter through the lesion so that the fins are aligned with the region of stenosis;

inflating the balloon so that the fins cut into the stenotic material;

deflating the balloon and subsequently re-inflating the balloon so that the fins cut further into the stenotic material.

In some cases the inflation and deflation steps are carried out multiple times as the balloon is located in the region of stenosis.

The method in some cases may comprise the step after angioplasty, deploying a stent at the lesion.

According to the invention there is provided an angioplasty balloon comprising:

an elongate tube of polymeric material having a relaxed delivery configuration and an expanded deployed configuration;

the elongate tube having fins which are integrally formed and which are spaced equidistant from one another about the exterior of the tube, with some of the fins selectively removed, the fins projecting radially outwardly from the exterior surface of the tube and the fins extending longitudinally along the tube when the tube is in the expanded configuration.

In one embodiment the tube comprises:

a man region;

a proximal neck portion;

a distal neck portion;

a tapered distal portion between the main region and the distal neck portion; and a tapered proximal portion between the main region and the proximal neck region.

In one embodiment there are only three fins which are preferably equi-spaced around the periphery of the balloon.

The invention also provides an angioplasty balloon comprising an elongate tube of polymeric material having a relaxed delivery configuration and an expanded deployed configuration, the elongate tube comprising:

a proximal neck portion;

a distal neck portion;

a main body region;

a tapered proximal portion extending between the main body region and the proximal neck portion; and a tapered distal portion extending between the main body region and the distal neck portion;

the elongate tube having only three fins which are integrally formed and which are spaced equidistant from one another about the exterior of the tube, and the fins projecting radially outwardly from the exterior surface of the body region of the tube.

In one embodiment the fins are shorter than the length of the body of the balloon, resulting in an un-finned area without any fins at each end of the balloon body.

In one embodiment the tips of the fins are rounded.

In one embodiment the tube is of a Nylon material such as Nylon 12.

There may be radiopaque marker bands to define the balloon body region, and additional marker bands to define the ends of the fins. In the preferred case there are 4 marker bands, two defining the balloon 'working length', and two defining the fin 'working length'.

Also provided is an angioplasty system comprising an angioplasty catheter having a balloon of the invention mounted thereto. There may be an inflation lumen for delivery of a medium for inflation of the balloon.

In another aspect the invention provides a method of treating a region of stenosis in a vasculature comprising the steps of:

providing an angioplasty system of the invention;

advancing the catheter to a lesion;

with the balloon in the relaxed configuration, advancing the catheter through the lesion so that the fins are aligned with the region of stenosis;

inflating the balloon so that the fins cut into the stenotic material;

deflating the balloon and subsequently re-inflating the balloon so that the fins cut further into the stenotic material.

In one case the inflation and deflation steps are carried out multiple times as the balloon is located in the region of stenosis.

In one use the method comprises, after angioplasty, deploying a stent at the lesion.

Thus according to a first aspect of the invention, there is provided a finned angioplasty balloon for an angioplasty balloon catheter. The finned angioplasty balloon is formed from an elongate polymer tube having only three fins projecting radially outward from the exterior surface of the tube and extending longitudinally along the entire length of the tube, such fins comprising the same polymeric material as the tube and formed integrally to the tube. Prior to forming the balloon sections of the fins may be selectively removed from the elongate polymer tube to result in the fins only being on the body portion of the formed balloon. The formed balloon is inflatable from a relaxed configuration to an expanded configuration.

The advantages of the three fin design are at least three-fold: the inflated 3 fin balloon will affect the full circumference of the vessel, impacting all of the lesion and importantly, the force is distributed equally over 3 sections of the lesion—causing less trauma than devices with only one or two scoring/cutting 'blades' and the three fins fold easily, allowing the uniquely low profile.

The advantages of the fins being shorter than the length of the balloon body include: the reduced profile of the distal un-finned area aids insertion of the balloon into the lesion being treated; the clinician can more easily avoid 'cutting' healthy vessel on either side of the lesion being treated; and the greater flexibility achieved by the shorter length fin results in improved deliverability of the angioplasty catheter.

Cutting balloons have higher wrapped profiles than equivalently sized standard PTA and PTCA catheters. The higher profile comes about because the blades/cutting surfaces of the cutting balloon have a volume that has to be accommodated in the wrapped profile. However, the use of the shorter fins of the invention in the central area of the balloon body only gives several advantages to achieving lower wrapped balloon profiles when compared to traditional cutting balloons. The advantages of the fins being shorter than the length of the balloon body include:

a) Lower wrapped profiles in the fin-free areas of the balloon body. The wrapped profile in these sections of the balloon will be equivalent to the profile of the same sections of a standard balloon of the same diameter. Of significance is that the balloon of the invention has lower wrapped profiles on the distal sections of the catheter (wrapped cone and distal fin-free area of the balloon body) which will allow for use with a similar size introducer sheath to a standard angioplasty balloon and also aids initial insertion of the finned device into the lesion to be treated.

b) A lower wrapped profile of the shorter finned section of the invention when compared to a more traditional cutting balloon that has the fins extending along the full length of the body, and beyond. In the case of the shorter fins of the invention, there is little or no tendency for the balloons to deform out of plane whilst being folded or wrapped, which will result in a lower wrapped profile for the finned section of the balloon. By comparison, where the blades/cutting surfaces found on traditional cutting balloons extend to, or cross over, the transition between balloon body and cone, there will be a tendency for the balloon and blade material to fold out of plane, causing discontinuities and a bunching effect. Because the blades have a volume, the bunching effect in the balloon body to cone transition area of the balloon is exaggerated, leading to a higher wrapped profile.

c) Another advantage of the shorter fins, coupled with the un-finned areas of the balloon body, is increased confidence that the fins will not impinge upon healthy vessel walls when the balloon is expanded in a lesion or stenosis. Accurate positioning of the balloon and fins is aided by the presence of marker bands in the balloon of the invention. Supported by fluoroscopic imaging capabilities, these marker bands aid the user in correctly positioning the balloon and fins in the lesion to be treated. The marker bands give clear information to the user about the balloon working length and the working length of the fins.

The presence of the fins on the balloon body will aid rewrap to a low profile following deployment of the balloon in the lesion being treated. This is because the fins will act as hinge points as the balloon is being deflated. With 3 fins around the circumference, the finned balloon will have a tendency to rewrap into a configuration with 3 wings.

The balloon comprises a conical distal end section (distal cone), a straight tubular middle section (main body of balloon) and a conical proximal end section (proximal cone), with the fins extending only along part of the main body of the balloon.

The fins are distributed evenly about the external circumference of the balloon so as to be equidistantly spaced apart.

Each fin has a substantially triangular cross-sectional shape in the form generally of an isosceles triangle with a radially outwardly projecting apex having a non-sharp, slightly rounded profile. The slightly rounded apex profile has the effect that when the balloon is expanded at the lesion site, the fin presses into the plaque and gently scores it rather than cutting sharply into it. It also minimises the risk of damage to the vessel wall through incision, dissection or perforation, by promoting the balloon to slide gently through the plaque as it is advanced or withdrawn, but not cut into the vessel wall.

The transition from the un-finned area of the balloon body to the fin apex can take various forms, including a step; a linear ramp; a concave ramp; or a convex ramp. The distal and proximal transitions of the fins can take different forms from one another. A preferred embodiment of the fins of the balloon of the invention is to have a leading (distal) edge which has a transition that comes to a point when meeting the apex of the fin, and a trailing (proximal) edge which has a seamless transition from apex to balloon body. The leading edge of the fin can ideally be a linear ramp or a concave ramp, and the trailing edge can be a convex ramp. A concave ramp on the leading edge of the fin is the preferred form as this will lead to a smoother transition from finned section of the balloon to non-finned section of the balloon.

Having the fins integrally formed on the balloon, which run along a portion of the balloon body can prevent the balloon from slipping off a lesion either as it is being inflated or when fully inflated in the vessel (melon seeding) and prevents the fins from detaching or becoming entrapped during angioplasty procedures. Fins which do not run along the entire length of the balloon will more easily 'anchor' into the calcified lesion which is being treated reducing the chance of melon seeding and ensuring only the calcified lesion will be treated as the physician has confidence as to the location of the start and finish of the fins. Therefore no healthy vessel will inadvertently be treated and potentially damaged by the clinician.

Three fins are spaced evenly around the circumference of the balloon, this allows for focal force along these three fins. Any additional fins around the circumference of the balloon would reduce the focal force along the additional fins and the already existing fins resulting in a less than desirable treatment. Alternatively two fins would give a higher focal force along the length of the fins however this would not treat the entire circumference of the lesion and therefore three fins are preferred. Additionally, three fins gives the maximum stability in terms of locating the fins relative to the vessel without compromising the force delivery.

The fins are radially stiff for optimum scoring of a heavily calcified lesion, but have sufficient longitudinal flexibility to facilitate ease of navigation to the treatment site, trackability through tortuous vessels and conformability to the vessel's natural curvature, while retaining sufficient longitudinal stiffness for optimum pushability for advancement of the device to the treatment site.

In a second aspect of the invention, there is provided a method for manufacturing the finned angioplasty balloon described herein, said method comprising the following steps:

(i) extruding a polymer material, preferably Nylon 12, using an extrusion die to form a tube in the desired shape and dimensions, incorporating fins of the desired shape and dimensions, equidistantly spaced on the surface of the extruded tube in the longitudinal direction.

(ii) stretching the extruded tube longitudinally in a hot bath at a set temperature by clamping one end and stretching using a set pressure and tension, followed by chilling the stretched tube in a cold bath;

(iii) selectively trimming the stretched tube to remove unwanted fin material. Removal can be achieved by various methods including grinding, laser ablation, hot wire cutting, skiving, or other; and (iv) blow-moulding the extruded stretched tube to form a balloon by supporting the tube in a stainless steel mould of the desired shape and dimensions and supplying pressurised gas to the interior of the tube to cause it to expand radially under controlled conditions of temperature and pressure for a controlled period of time and form a balloon in the shape and dimensions of the inner surface of the mould. The extruded stretched tube is expanded such that the internal diameter of a portion of the tube (i.e. the balloon middle section) increases approximately fivefold.

In one case, the extruded tube comprises of polyamide (Nylon 12). Nylon 12 is a high strength material with ability to hold its shape during the balloon blowing processing. Other suitable materials for the balloon of the invention include, but are not limited to, PEBAX, polyethylene terephthalate (PET), polyurethane and blends of these materials, possibly also including Nylon 12.

The stretching process is used to align the molecules of the extruded tube longitudinally, such that if the resulting balloon is to burst upon inflation subsequent to the manufacturing process, it will burst in a longitudinal manner and not in a radial manner. The stretching process will reduce the cross-section of the extruded tube, as well as reducing the size of the fins. The extrusion and stretching steps combine together to determine the final height of the fins.

The fins are designed to withstand deformation during the stretching and blow moulding processes so that a significant portion of the fin does not become absorbed into the wall of the balloon when the radial expansion occurs during the blow moulding process, thereby retaining the structural shape and dimensions of the fins.

The integral fins are generally triangular in shape, with a height of about 0.75 mm, or less. The triangular shape of the fin is chosen to give optimal scoring performance when the balloon is deployed in the vessel to be treated. With the balloon inflated, the triangular form of fin gives an ideal combination of stability when being offered up to the vessel wall, and the tip of the triangular fin allows force to be focused on the part of vessel directly in contact with the fins. The fins have a base width of about 0.5 mm, or less. The width of each of the fins is less than the height of the fins, with a ratio of the height of the fins to their base width of the order of about 1.25:1 to 1.75:1. The narrower base width assists in achieving reduced folded profile of the balloon, with integral fins, for more effective delivery of the scoring balloon to the treatment site.

Also provided is a finned angioplasty balloon catheter device having a balloon of the invention mounted thereto. The catheter incorporates a co-axial shaft comprising an inner lumen which passes through the balloon for insertion of a guidewire, surrounded by an outer lumen terminating in the proximal sleeve of the balloon for delivery of an inflation medium into the balloon; the inner lumen terminating in a soft tip at the distal end of the balloon, through which the guidewire passes and which forms the leading edge of the device. The catheter also incorporates a manifold or hub in a Y shape at the proximal end of the catheter shaft with two insertion ports, one for insertion of the guidewire and one for insertion of the inflation medium. The catheter further incorporates marker bands to define the balloon and optionally the fin working lengths, with marker bands positioned at each of the proximal end and the distal end of the main body of the balloon, and optional marker bands positioned at each end of the fins. The balloon is optionally coated with a hydrophilic coating for lubricity and is folded and wrapped onto the catheter shaft, with the fins extending radially from the catheter shaft in the folded state. The above describes an Over-The-Wire catheter configuration. Other catheter configurations that the balloon of the invention can be mounted onto include Rapid Exchange/Monorail configurations, and fixed wire configurations.

The finned angioplasty balloon catheter device may be provided in a range of balloon lengths and diameters and overall catheter lengths, preferably in balloon lengths of 20 mm to 300 mm, balloon diameters of 1.5 mm to 12 mm and overall catheter lengths of 450 mm or longer, for both coronary and peripheral vascular angioplasty procedures. This represents a significant improvement over the range of sizes offered by currently available cutting/scoring angioplasty balloons. This wide matrix of sizes addresses the specific requirements of peripheral vascular interventions, in particular for complex, below-the-knee procedures, which demand low profile, longer balloons.

The profile, or outer diameter, of the finned angioplasty balloon catheter device, when in its folded state prior to insertion, will be the same or only marginally greater than an equivalent sized standard angioplasty balloon dilatation catheter. Using the French catheter sizing system that is used in the industry—in the case of the 0.018" (0.4572 mm) guidewire compatible device format, this will comprise preferably 4Fr (=1.33 mm), 5Fr (=1.67 mm), and 6Fr (=2.00 mm) sizes. This represents a significant breakthrough over currently available cutting/scoring angioplasty balloons, which are generally only available in 6Fr and larger sizes. The lower profile is achieved by combining a thin-wall, single-layer polymeric balloon material, with fins comprising the same polymeric material integrally formed as part of the balloon extrusion, fin design, fins of length shorter than the balloon body and moulding processes. The moulded balloon is subsequently folded and wrapped on a co-axial catheter shaft using a 3 pleat folding and compression process.

The finned angioplasty balloon catheter device demonstrates longitudinal flexibility equivalent to standard angioplasty balloon catheters, thereby facilitating ease of navigation to the treatment site, trackability through tortuous vessels and conformability to the vessel's natural curvature, while retaining sufficient longitudinal stiffness for optimum pushability for advancement of the device to the treatment site. This represents a significant breakthrough over current cutting/scoring angioplasty balloons, which limit the flexibility of the device.

In another aspect of the invention, there is provided a method of use of the finned angioplasty balloon catheter for scoring and dilating hardened or calcified lesions/stenosis in the coronary or peripheral vasculature and/or in performing vessel preparation for subsequent drug delivery by means of a drug coated balloon in the coronary or peripheral vasculature.

In one embodiment of the method the finned angioplasty balloon is inflated radially at the site of a calcified lesion/stenosis, whereupon the fins act as pressure points or disruptive edges pressing into the calcified plaque causing it to score, or crack, thereby facilitating successful dilatation of the vessel by the inflated balloon; this embodiment comprises the following steps:

(i) providing a finned angioplasty balloon catheter of the invention;
(ii) introducing a guidewire through an introducer sheath inserted in the femoral or radial artery, and advancing the wire to the site of a lesion in a coronary or peripheral artery;
(iii) loading the catheter onto the wire and feeding the catheter to the vasculature through the introducer;
(iv) advancing the catheter to the lesion, whereby the low profile tip and low profile distal un-finned area of the balloon will facilitate the advancement of the balloon through the lesion.
(v) positioning the balloon optimally across the lesion, whereby the balloon body marker bands indicate that the working length of the balloon is aligned with the region of stenosis, and the optional fin markers indicate that the central area of the lesion will be impacted by the cutting/scoring action of the fins when the balloon is deployed;
(vi) inflating the balloon to its rated nominal pressure, whereby as the balloon expands, the fins on the main body of the balloon press into and score, or crack, the stenotic material, thereby allowing the balloon to fully expand and dilate the stenosed artery;
(vii) deflating the balloon and withdrawing the catheter and the guidewire from the vasculature.

In another embodiment the method may comprise delivering and inflating the balloon as described above, then deflating the balloon and subsequently re-inflating the balloon in the same position as before, whereby the fins further score the stenotic material and the balloon further dilates the stenosed artery.

In another embodiment the method may comprise deflating the balloon, advancing or withdrawing the catheter slightly to change the precise position of the balloon and subsequently re-inflating the balloon so that the fins cut into the stenotic material in a different location or orientation;

In another embodiment of the method the inflation and deflation steps are carried out multiple times as the balloon is located in the region of stenosis.

In a further embodiment of the method, the finned angioplasty balloon is deployed to prepare a stenosed blood vessel in the coronary or peripheral vasculature for subsequent drug treatment using a drug coated balloon or a drug eluting vascular scaffold; whereby the finned angioplasty balloon is inflated radially at the site of a calcified lesion/stenosis, whereupon the fins act as pressure points or disruptive edges pressing into the calcified plaque causing it to score, or crack, in multiple locations about the inner lumen of the vessel, thereby creating multiple pathways or channels for subsequent absorption of a drug into the stenosed vessel wall upon delivery to the site using a drug coated balloon or a drug eluting bioresorbable vascular scaffold.

BRIEF DESCRIPTION OF THE DRAWINGS

The invention will now be described with reference to the accompanying drawings which show embodiments of the finned angioplasty balloon according to the invention in which.

DETAILED DESCRIPTION

Figure 1:
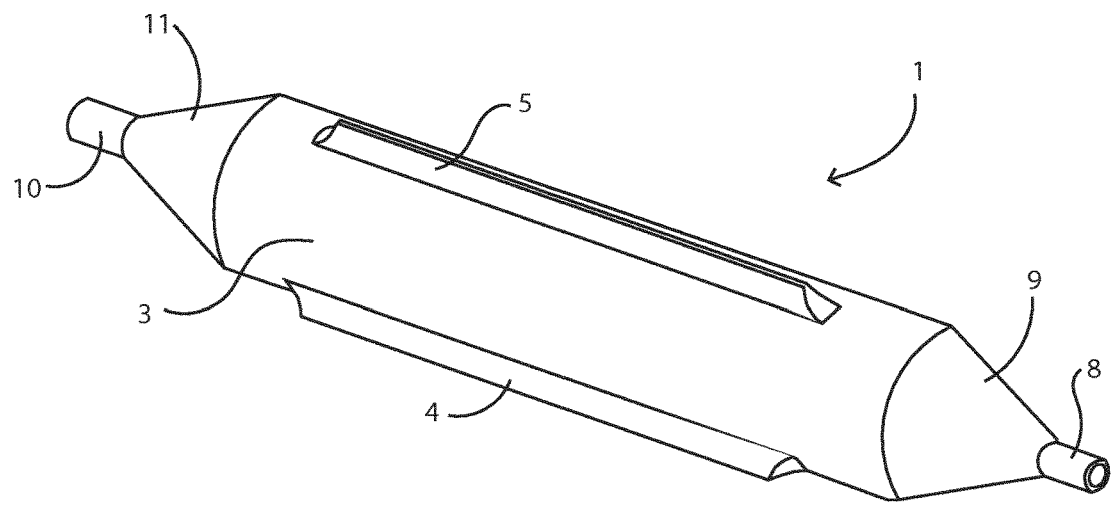
FIG. 1 is a perspective view of a finned angioplasty balloon according to the invention.

Referring to the Figures, FIG. 1 shows an angioplasty balloon according to the invention, generally indicated by reference numeral 1, the finned angioplasty balloon being for use with a catheter (not shown) and comprising an elongate extruded tube having an expandable balloon region 3 and three fins 4, 5 (shown) and 6 (hidden) extending along part of the length of the balloon body section and projecting radially outwardly from the exterior surface of the balloon body. The tube also has a distal neck portion 8, a tapered distal end region 9, a proximal neck 10, and a tapered proximal end region 11.

Figure 8:
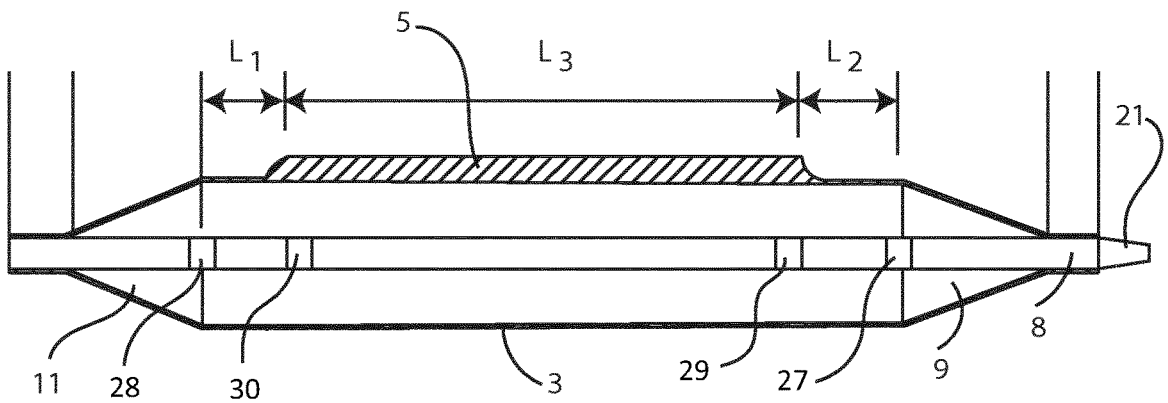
FIG. 8 is a cross-sectional view of a finned angioplasty balloon according to the invention.

Referring in particular to FIG. 8, the fin-free proximal region of the main body has a length $L_1$ of from 0.6 to 1.2 times the nominal diameter of the balloon, preferably about 0.8 or 0.75 times the nominal diameter of the balloon.

The fin-free distal region of the main body has a length $L_2$ of from 0.6 to 1.2 times the nominal diameter of the balloon, preferably about 0.8 or 0.75 times the nominal diameter of the balloon.

The length $L_3$ of the fin preferably equals the balloon nominal length minus about one and a half times the balloon nominal diameter. The nominal diameter and nominal length for a given balloon are achieved when the balloon is inflated to nominal pressure. The following table gives some examples.

We have found that the fin free proximal and distal regions of the main body of the balloon are optimally in the ratios outlined above in order to maximise the effective scoring/cutting capability of the balloon fins whilst minimising the overall profile of the balloon.

As an example, a balloon of the invention with a nominal 8.0 mm diameter balloon, and a nominal balloon body of 60 mm length, would have fins with a length of 48 mm, and fin free sections at each end of the balloon of 6 mm from the end of the fin to the balloon body to cone transition.

As another example, a balloon of the invention with a nominal 6.0 mm diameter balloon, and a nominal balloon body of 40 mm length, would have fins with a length of 30 mm, and fin free areas at each end of the balloon of 5 mm.

| Scoring Balloon diameter × length | Balloon OD at Nominal Pressure such as 8 Atm | Balloon Length at Nominal Pressure such as 8 Atm | Scoring Fin Length at Nominal Pressure such as 8 Atm |
| --- | --- | --- | --- |
| 4.0 mm × 40 mm | 4.00 mm | 40 mm | 34 mm |
| 5.0 mm × 60 mm | 5.00 mm | 60 mm | 52 mm |
| 6.0 mm × 80 mm | 6.00 mm | 80 mm | 71 mm |

Limiting the fins to the body section of the balloon, and having an un-finned portion at either end of the balloon body aids the insertion of the balloon through a region of stenosis.

The three fins 4, 5, 6 run along part of the length of the balloon body 1 and are spaced equidistant from one another longitudinally about the exterior surface of the balloon outer circumference. The fins 4, 5, 6 have longitudinal axes which are arranged parallel to the longitudinal axis of the balloon. As shown in FIG. 1, the balloon 1 has the form of the balloon immediately on manufacture. This is in an inflated state. In later manufacturing steps, this balloon is folded into a more compact radial dimension for storage and delivery to a treatment site in a patient's body, usually by the balloon being deflated and with folds formed in it about the longitudinal axis.

Each fin has a substantially triangular cross-sectional shape in the form generally of an isosceles triangle with a radially outwardly projecting apex having a non-sharp, slightly rounded profile. The slightly rounded apex profile has the effect that when the balloon is expanded at the lesion site, the fin presses into the plaque and gently scores it rather than cutting sharply into it. It also minimises the risk of damage to the vessel wall through incision, dissection or perforation, by promoting the balloon to slide gently through the plaque as it is advanced or withdrawn, but not cut into the vessel wall.

The integral fins are generally triangular in shape, with a height of about 0.75 mm, or less. The triangular shape of the fin provides optimal scoring performance when the balloon is deployed in the vessel to be treated. With the balloon inflated, the triangular form of fin gives an ideal combination of stability when being offered up to the vessel wall, and the tip of the triangular fin allows force to be focused on the part of vessel directly in contact with the fins.

The fins have a base width of about 0.5 mm, or less. The width of each of the fins is less than the height of the fins, with a ratio of the height of the fins to their base width of the order of about 1.25:1 to 1.75:1. These dimensions ensure that desirable scoring/cutting force at the treatment site is achieved. The narrower base width also assists in achieving reduced folded profile of the balloon, with integral fins, for more effective delivery of the scoring balloon to the treatment site In known manner, the balloon catheter is delivered to the treatment site using the standard visualisation techniques such as radiopaque marking and/or radiopaque dye. When the expandable main balloon region 3 is positioned in place at the site of the stenosis, an inflation medium is supplied to the expandable balloon region 3 to expand the balloon, causing the expandable balloon portion 3 to impinge on the vessel wall. At the same time, the fins 4, 5, 6 which are formed integrally with the wall of the balloon move radially outwardly until their apices, which are ideally rounded to a small radius, are pressed against and into the hardened deposits at the stenosed site. Thus, the fins 4, 5, 6 assist in opening up the hardened deposits facilitating the balloon to expand to the desired size to clear the stenosis.

Figure 2:
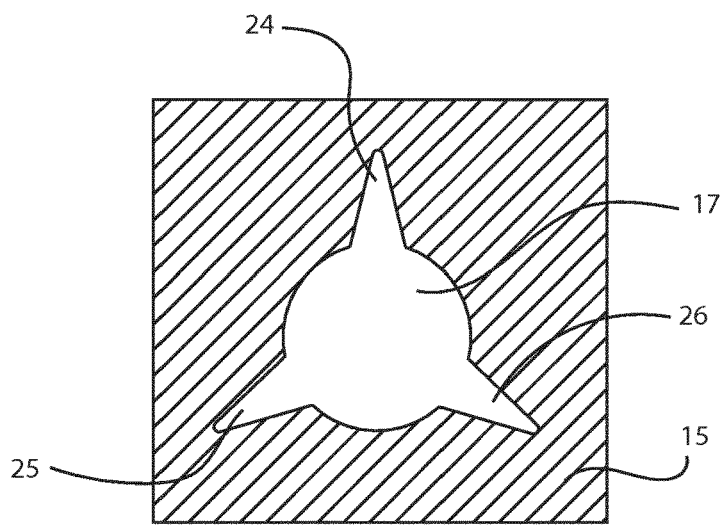
FIG. 2 is a cross-sectional view of a die shape for extruding a tube for a preferred finned angioplasty balloon according to the invention.

FIG. 2 shows a cross-sectional view of a die 15 used to form an extruded tube 16 which is later formed into balloon 1. Die 15 includes a cavity 17 which is sized and shaped to enable an extruded tube 16 to be extruded therefrom, initially as a hollow tube. Thus, cavity 17 has a central circular shape with three radiating arms 24, 25 and 26 which are adapted to enable fins 4, 5, 6 respectively to be extruded therefrom.

In the extrusion process pellets of the polymeric plastics material for forming the tube 16 are cleaned, dried, and placed into an extruder. Tubing of the desired shape is formed, and then cooled and solidified as it passes through the air and passed into a water bath. The size of the tubing is determined by the die dimensions and the drawdown that occurs with tension on the extrudate.

Figure 3:
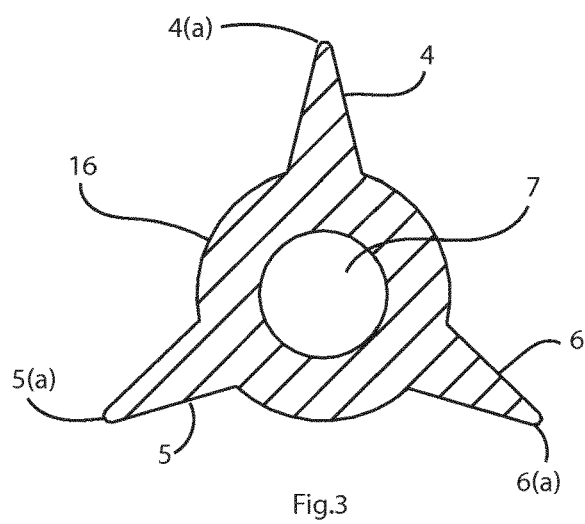
FIG. 3 is a cross-sectional view of the extruded tube for making a preferred finned angioplasty balloon according to the invention prior to stretching and moulding the tube into a balloon by longitudinal stretching and expansion.

At this stage, the extruded tube has the cross-sectional appearance of the tube shown in FIG. 3 with central lumen 7, balloon wall portion 16 and radiating fins 4, 5, 6.

The next step of the manufacturing process is a stretching step. The intent of the stretching step is to mechanically stretch the polymer chains of tube 16 so that they provide maximum strength to the extruded balloon as well as resisting further growth. Important inputs in this process are pressure applied during stretching, hot and cold bath temperatures and the distance that the tube is stretched, and these parameters will be selected depending on the polymeric material being used for a particular balloon.

Figure 4:
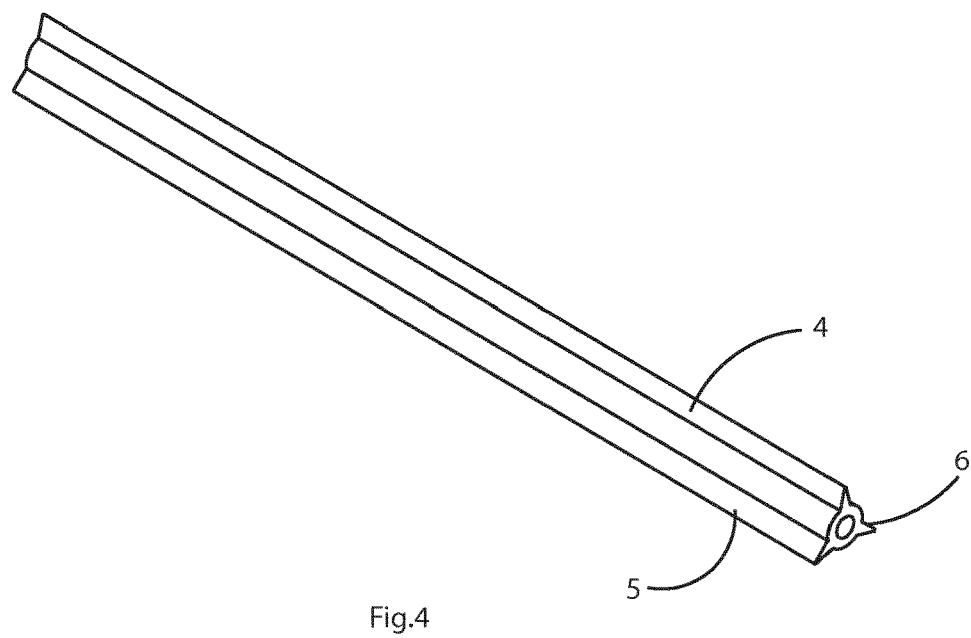
FIG. 4 is an isometric view of the extruded tube, following stretching to reduce the cross section.
Figure 5:
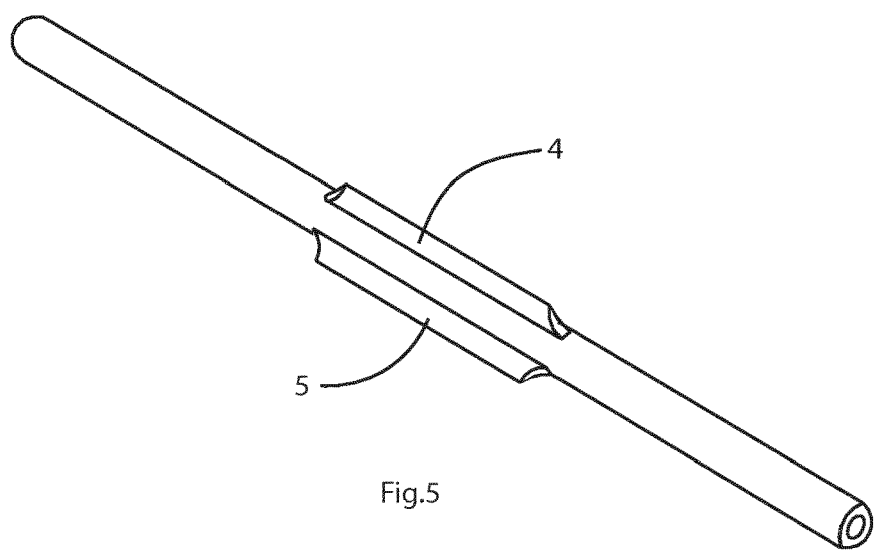
FIG. 5 is an isometric view of the extruded tube, following stretching and selective removal of fins.

The stretched tube is then processed to selectively remove fins from parts of the tube where they're not required for the finally formed balloon. This process can take many forms including laser ablation, grinding away excess material, removal of material using a hot-wire or hot-knife, or using a blade to skive away unwanted material. FIG. 4 shows the stretched extruded tube, and FIG. 5 shows the stretched extruded tube with fins selectively removed to leave fins 4, 5 and 6 in place. Some fin sections, though not needed for the finally formed balloon, may be kept in place to aid later processing steps. These fin sections could, for example, be used to ensure correct alignment, in both the circumferential and longitudinal directions, of the fins 4, 5 and 6 in the balloon mould.

In the next step, the stretched tube 16 is then pressurized in a mould while being subjected to elevated temperatures. This process results in the blowing/moulding of the tube into the desired balloon shape.

The moulding process uses the three variables, heat, pressure and time to form the balloons. Again, the specific parameters will be selected depending on the polymeric material being used. The overall process consists of pressurising a stretched tube and dipping the tube into a heat source. When the modulus of elasticity of the material falls below the moulding stress being applied the balloon 1 forms. The modulus of the material diminishes with time due to the increase in temperature of the polymeric material. The formation of the balloon is rapid due to the fact that using a constant moulding pressure is used. As the stretched tube softens with the heat that is being applied (and the modulus of elasticity of the material diminishes) the pressure blows the stretched tube outwardly against the interior walls of the mould.

Figure 6:
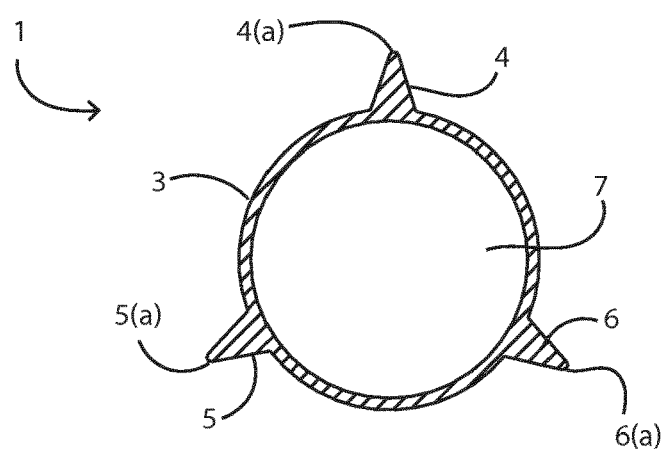
FIG. 6 is a cross-sectional view of the body of a finned balloon formed from the extruded tube shown in FIGS. 3, 4, and 5 after stretching and radial expansion.

At the end of the moulding process, the wall of the balloon portion 3 have expanded radially outwardly. By comparing FIGS. 3 and 6, it can be seen that the stretching and blow moulding steps cause the wall 3 of the balloon to become thinner, the lumen 7 to become about 5-fold larger in diameter and the fins 4, 5, 6 to broadly maintain their original form. A rounded apex profile 4a, 5a, 6a of the fins 4, 5, 6 is retained throughout.

The balloon is then ready for downstream processing steps such as for example the mounting onto a catheter, balloon folding, receipt of a guidewire into the lumen 30 or the like.

Many materials which are suitable for use in the manufacture of balloons for angioplasty catheters are equally suitable for manufacture of the balloon of the present invention. What is important is that the material is such that the fins, formed on the balloon are sufficiently flexible to enable the balloon to track through tortuous body vessels, yet resilient enough so that the fins can be pressed into hardened sclerotic deposits at a treatment site so as to open-out the deposits. One suitable material for these purposes is Nylon 12—a relatively soft material, allowing a low folded profile and the 'softness' helping to reduce the risk of vessel trauma.

Figure 7:
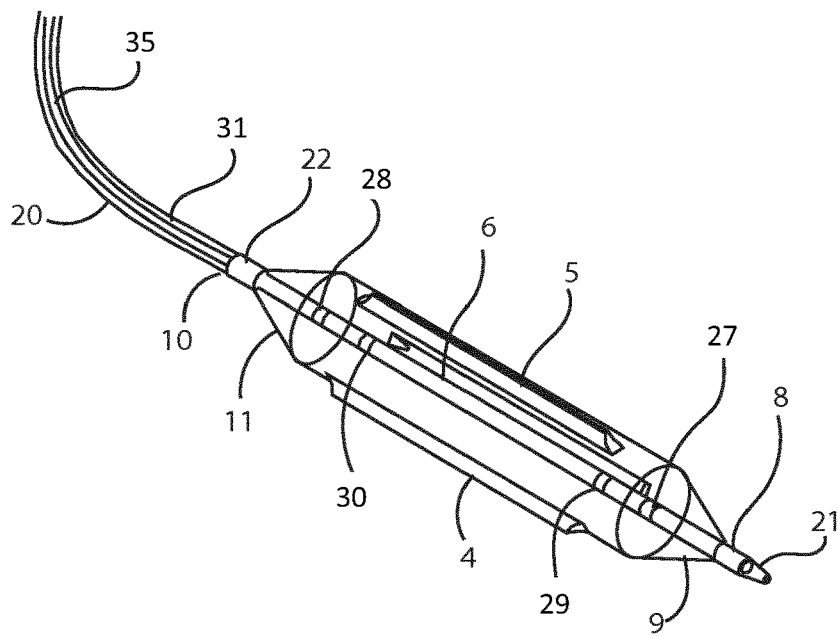
FIG. 7 is a perspective view of the balloon on a catheter according to the invention.

Referring to FIG. 7, the angioplasty balloon according to the invention is illustrated mounted on an angioplasty catheter having an outer 20 and an inner 35. The catheter has a soft distal tip 21. The balloon is joined to the outer 20 at a proximal bond section 22.

The inner 35 of the catheter has marker bands 27, 28, 29, and 30, (respectively demarking the distal and proximal ends of the balloon body, and the distal and proximal ends of the fins), and defines a passageway for tracking over a guidewire (not shown). The marker bands 27, 28, 29, and 30 are a visualisation aid to the physician for accurate positioning of the balloon and fins relative to the lesion being treated in the procedure. The guidewire passes through a guidewire lumen at the proximal end of the catheter. The gap 31 between the inner, 20, and outer, 30, defines a passageway for delivery of an inflation medium from an inflation lumen at the proximal end of the catheter.

Figure 9:
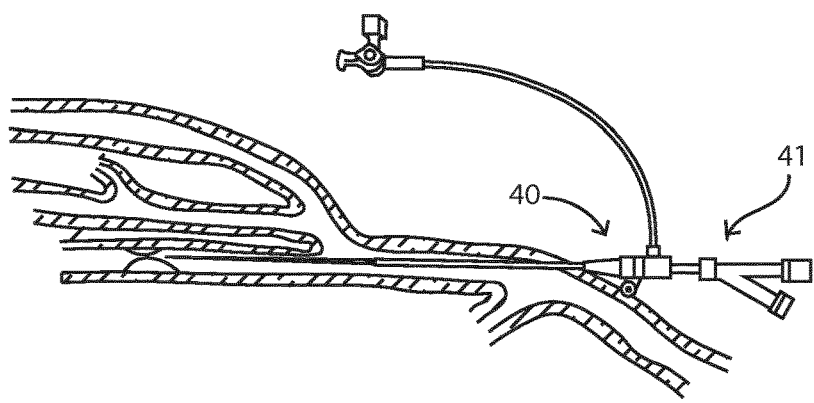
FIG. 9 illustrates typical femoral access approach used for carrying out a procedure on a patient.
Figure 10:
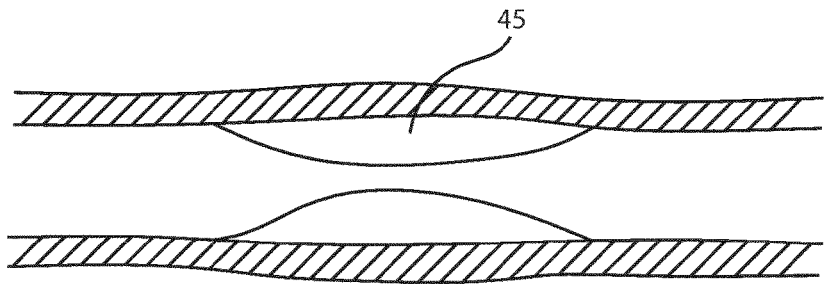
FIG. 10 is an illustration of a region of stenosis in a vasculature.
Figure 11:
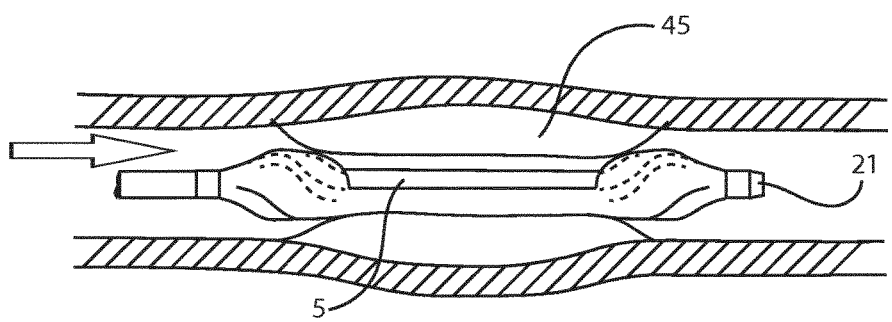
FIGS. 11 to 15 illustrate various steps in a method for treatment of the stenosis using the finned angioplasty balloon catheter device of the invention.

FIG. 9 illustrates a typical introducer 40 which is used to gain access to the vasculature, for example using a femoral approach as illustrated. An angioplasty catheter 41 is then advanced through the guide catheter towards a lesion or region of stenosis 45 as diagrammatically illustrated in FIG. 11.

Figure 12:
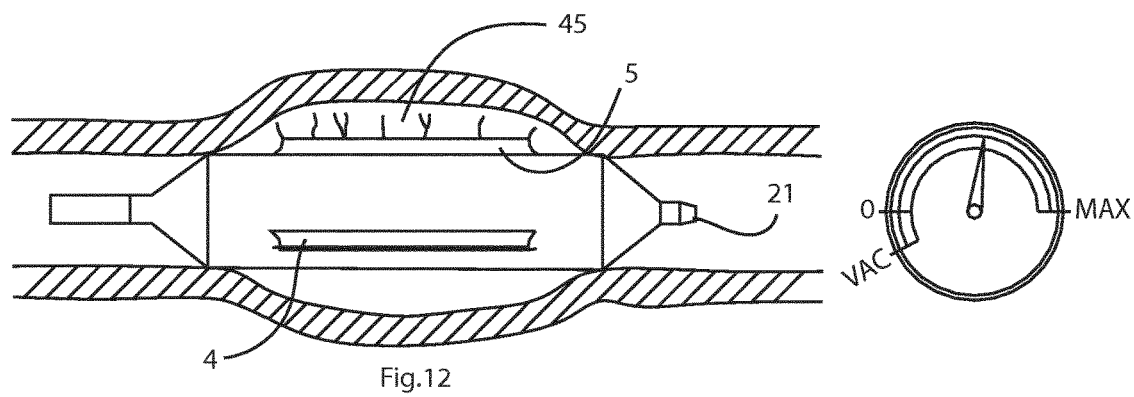
Figure 13:
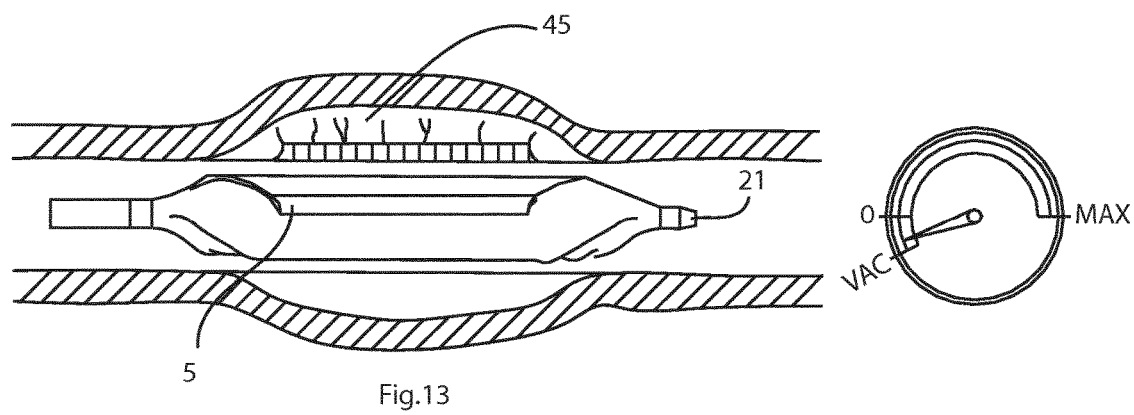
Figure 14:
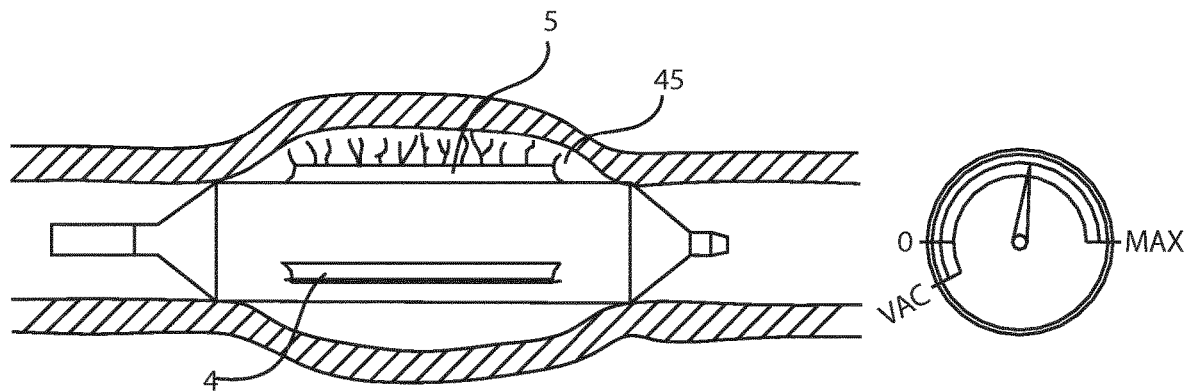
Figure 15:
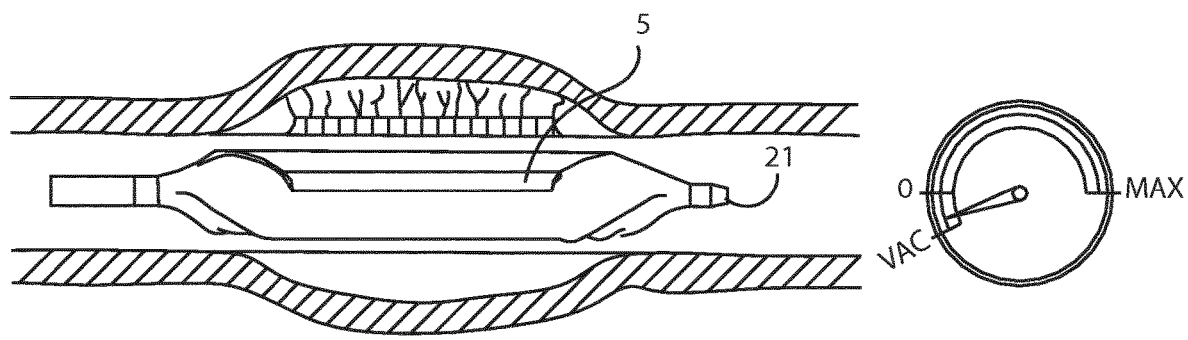
Figure 16:
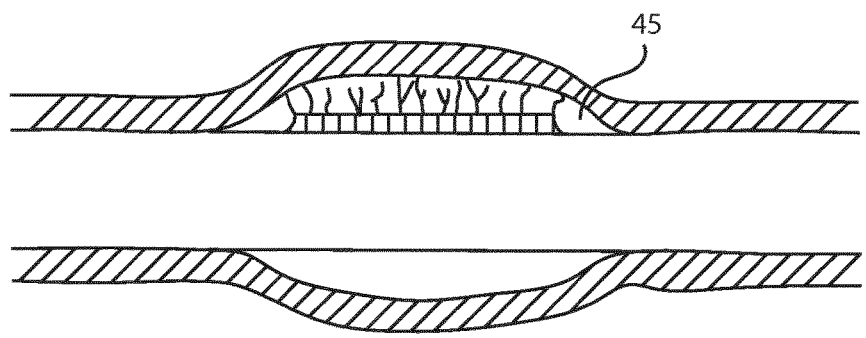
FIG. 16 is an illustration of a region of stenosis treated using the finned angioplasty balloon catheter device of the invention.
Figure 17:
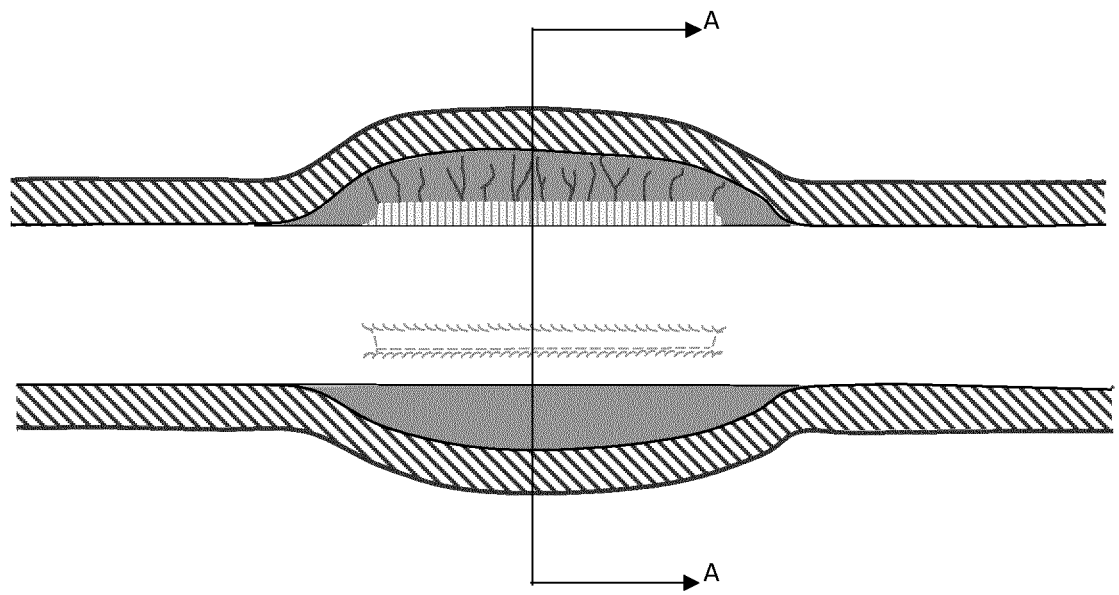
FIG. 17 is another view of a region of stenosis treated using the finned angioplasty balloon catheter device of the invention.
Figure 18:
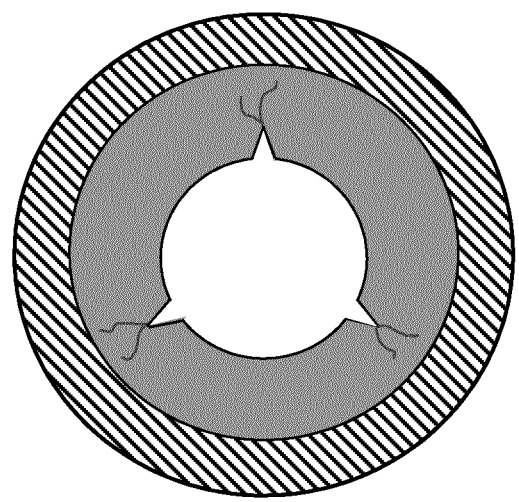
FIG. 18 is a cross-sectional view on the line A-A of FIG. 17.

The balloon is then inflated (FIG. 12), and subsequently deflated (FIG. 13). During the inflation/deflation cycles, which may be repeated several times (FIGS. 14 & 15), the fins aid the break-up of the stenotic material and opening up the vasculature (FIGS. 16 to 18) at the region of stenosis. In some cases, a stent may be deployed to assist in reinforcing the vessel at the lesion and/or for drug delivery.

The finned balloon of the invention is particularly useful in treatment of a tight stenosis. In this case the balloon is inflated, deflated, advanced and re-inflated several times.

The ability of the balloon to advance effectively to the treatment site (lesion or stenosis) is determined by a number of factors including the wrapped balloon profile. Because of the presence of the fins on the body of the balloon, the wrapped profile of a finned balloon will be somewhat greater than that of an identical sized balloon with no fins. However, with the balloon of the invention, the presence of an un-finned portion in the distal section of the balloon body means that the balloon will have a crossing profile that steps up in size from distal to mid-section of the balloon body. The gradual step-up in size of the balloon from distal tip to finned section will facilitate the advancement of the balloon into tighter lesions.

When a standard balloon is repeatedly inflated and deflated the balloon will lose it memory to rewrap. The presence of the fins in the balloon of the invention will aid the balloon in keeping its memory and its ability to rewrap.

The fins on the balloon of the invention aid in advancing through the lesion, in its deflated state, as there is less contact between the balloon and lesion and in turn less friction. This is because the balloon is running on the reinforced fins. The fins on the balloon of the invention also add to the column strength of the folded balloon, facilitating more push on the catheter to insert through the lesion.

Similarly, after the balloon has been used to treat the lesion, the withdrawal force to remove the catheter, in its deflated state, will be reduced due to a reduction in contact with the vessel/lesion.

Figure 19:
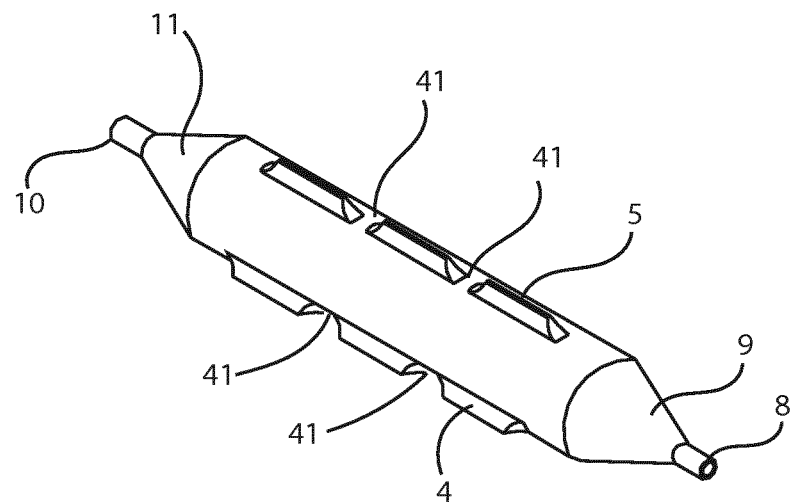
FIG. 19 is a perspective view of another finned angioplasty balloon according to the invention.

FIG. 19 illustrates another angioplasty balloon according to the invention which is similar to the balloon described with reference to FIGS. 1 to 18 and like parts are assigned the same reference numerals. In this case the fins 4, 5, 6 (hidden) have interruptions 41 which are of smooth profile. The interruptions 41 are designed to aid flexibility in tortuous vessels, the interruptions help the inflated balloon to bend and conform to vessel walls, reducing the risk of trauma.

Figure 20:
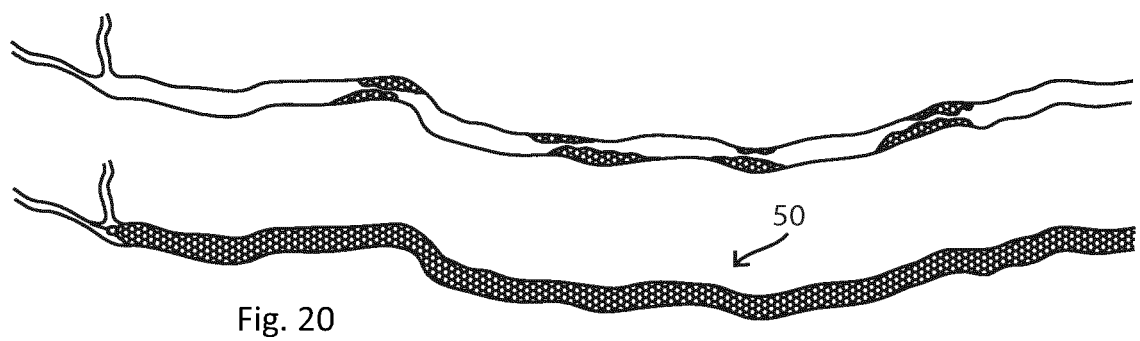
FIGS. 20 to 22 are images illustrating the use of a long finned angioplasty balloon device according to the invention, in treating multiple lesions.
Figure 21:
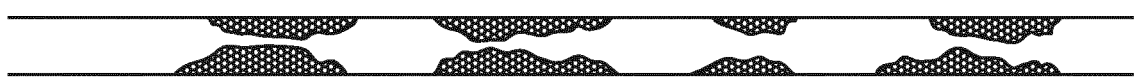
Figure 22:
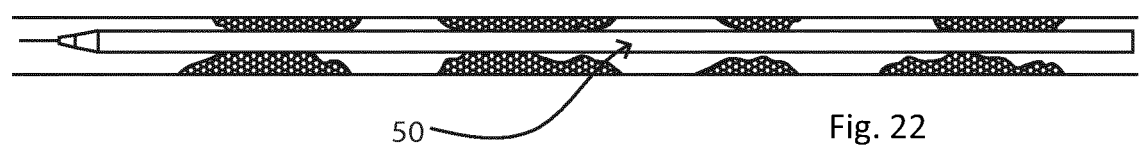

FIGS. 20 to 22 show a long length balloon 50 of the 3 fin design balloon—experienced clinicians prefer to use a single inflation long balloon for procedural speed and to help reduce the risk of vessel trauma, especially when treating multiple lesions. The balloon 50 may, for example, be greater than 250 mm long.

It will of course be understood that the invention is not limited to the specific details as herein described, which are given by way of example only, and that various alterations and modifications are possible without departing from the scope of the invention.

The invention claimed is:

1. An angioplasty balloon comprising:
an elongate tube of polymeric material having a relaxed delivery configuration and an expanded deployed configuration, the elongate tube comprising:
a main body portion; and
a plurality of radially extending fins, formed integrally with the elongate tube, each fin extending substantially from a first longitudinal end to a second longitudinal end of the main body portion along a central part of the main body portion when the tube is in the expanded deployed configuration,
each fin comprising a radially outwardly projecting apex comprising a non-sharp profile configured to press into surrounding material when in the expanded configuration,
wherein each fin comprises a first end which is of a generally concave shape in the longitudinal cross section and a second end which is of a generally convex shape in the longitudinal cross section.

2. The angioplasty balloon of claim 1, wherein a proximal region of the main body has a length of 0.6 to 1.2 times a nominal diameter of the angioplasty balloon.

3. The angioplasty balloon of claim 1, wherein a distal region of the main body has a length of 0.6 to 1.2 times a nominal diameter of the angioplasty balloon.

4. The angioplasty balloon of claim 1, wherein a length of at least one fin equals an angioplasty balloon nominal length minus about one and a half times an angioplasty balloon nominal diameter.

5. The angioplasty balloon of claim 1, wherein a height of each of the fins is about 0.75 mm or less.

6. The angioplasty balloon of claim 1, wherein a width of each of the fins, at its widest point, is about 0.5 mm or less.

7. The angioplasty balloon of claim 1, wherein a ratio of the height of the fins to a width of a base of the fins is from about 1.25:1 to about 1.75:1.

8. The angioplasty balloon of claim 1, wherein the plurality of fins comprises three fins.

9. The angioplasty balloon of claim 1, wherein the fins have longitudinally spaced-apart interruptions.

10. An angioplasty system, comprising:
the angioplasty balloon of claim 1; and:
a catheter to which the angioplasty balloon is mounted, the catheter comprising:
an outer shaft to which a proximal end of the angioplasty balloon is mounted and an inner shaft which extends through the angioplasty balloon wherein the inner shaft has at least one radiopaque marker band thereon aligned with a fin-free proximal or distal region of the main body portion of the angioplasty balloon.

11. The angioplasty system of claim 10, wherein the inner shaft has a distal marker band aligned with the fin-free distal region of the main body portion of the angioplasty balloon and a proximal marker band aligned with the fin-free proximal region of the main body portion of the angioplasty balloon.

12. The angioplasty balloon of claim 1, wherein the radially outwardly projecting apex of each of the fins extends in a linear direction that is parallel to a longitudinal axis of the balloon.

13. The angioplasty balloon of claim 1, wherein the radially outwardly projecting apex of each of the fins is a furthest edge radially from a longitudinal axis of the balloon.

14. An angioplasty balloon comprising:
an elongate tube of polymeric material having a relaxed delivery configuration and an expanded deployed configuration, the elongate tube comprising:
a main body portion; and
a plurality of radially extending fins formed integrally with the elongate tube, each fin extending substantially from a first longitudinal end to a second longitudinal end of the main body portion along a central part of the main body portion when the tube is in the expanded deployed configuration,
wherein each fin comprises a distal end which is of a generally concave shape in the longitudinal cross section and a proximal end which is of a generally convex shape in the longitudinal cross section.

15. The angioplasty balloon of claim 14, wherein the fins have longitudinally spaced-apart interruptions.

16. The angioplasty balloon of claim 14, wherein a ratio of the height of the fins to a width of a base of the fins is from about 1.25:1 to about 1.75:1.

17. The angioplasty balloon of claim 14, wherein a distal region of the main body has a length of 0.6 to 1.2 times a nominal diameter of the angioplasty balloon.

18. The angioplasty balloon of claim 14, wherein a length of at least one fin equals an angioplasty balloon nominal length minus about one and a half times an angioplasty balloon nominal diameter.

19. An angioplasty system, comprising:
the angioplasty balloon of claim 14;
a catheter to which the angioplasty balloon is mounted, the catheter comprising:
an outer shaft to which a proximal end of the angioplasty balloon is mounted and an inner shaft which extends through the angioplasty balloon wherein the inner shaft has at least one radiopaque marker band thereon aligned with a fin-free proximal or distal region of the main body portion of the angioplasty balloon.

* * * * *